United States Patent [19]
Gilbert

[11] Patent Number: 4,951,482
[45] Date of Patent: Aug. 28, 1990

[54] HYPOTHERMIC ORGAN TRANSPORT APPARATUS

[76] Inventor: Gary L. Gilbert, 4350 Troost, #4, Studio City, Calif. 91604

[21] Appl. No.: 288,776
[22] Filed: Dec. 21, 1988
[51] Int. Cl.⁵ .............................................. F25D 3/08
[52] U.S. Cl. .................................... 62/457.1; 62/306; 62/463
[58] Field of Search ....................... 62/306, 463, 457.1
[56] References Cited

U.S. PATENT DOCUMENTS

| | | | |
|---|---|---|---|
| 1,369,367 | 2/1921 | Thomson | 62/463 X |
| 3,777,507 | 12/1973 | Burton et al. | 62/306 |
| 3,810,367 | 5/1974 | Peterson | 62/463 X |
| 3,914,954 | 10/1975 | Doerig | 62/306 |
| 3,995,444 | 12/1976 | Clark et al. | 62/306 |
| 4,242,883 | 1/1981 | Toledo-Pereyra | 62/306 |
| 4,462,215 | 7/1984 | Kuraoka et al. | 62/306 X |
| 4,494,385 | 1/1985 | Kuraoka et al. | 62/306 |
| 4,502,295 | 3/1985 | Toledo-Pereyra | 62/463 |
| 4,530,816 | 7/1985 | Douglas-Hamilton | 62/463 X |

Primary Examiner—Lloyd L. King
Attorney, Agent, or Firm—Roger A. Marrs

[57] ABSTRACT

A portable container is disclosed herein for the hypothermic transport of donor organs which includes an inner container holding a body organ within a surrounding preservation medium and an outer container suspending the inner container within a thermoregulatory fluid. The inner and outer sidewalls are transparent, permitting exterior stored organ visual inspection. An air inlet exhaust port is provided on the outer container for controlling the volume of fluid into which the organ-carrying inner container is held. The double container storage, storage medium and fluid, as well as proper sealing devices, provide for sterile isolation of the organ.

3 Claims, 2 Drawing Sheets

HYPOTHERMIC ORGAN TRANSPORT APPARATUS

BACKGROUND OF THE INVENTION

1. Field of the Invention

The present invention relates to transportation systems and apparatus, and more particularly to a disposable medical container for the hypothermic transport of donor organs used for transplantation medical procedures.

2. Brief Description of the Prior Art

In the past, it has been the conventional procedure to remove a donor organ, such as a kidney, heart or the like, followed by storage of the organ in an iced container which is then transported to another location for implantation into the body of a recipient. This procedure requires manual handling or manipulation of the organ followed by introduction of the organ into the storage container and subsequent removal of the organ from the container preparatory for the transplantation. A sterile environment during storage as well as during the handling of the organ is of utmost concern and maintenance of a proper temperature of tissues during transport is required in order to maintain tissue integrity. Various storage containers have been provided for shipping or transporting the removed organ from place to place and generally take the form of expensive and complex arrangement of compartments for holding the organ, receiving a cooling medium, such as ice, and for handling the container after storage of the organ. Such a container is not disposable and does not permit visual inspection of the organ either during transportation or at the site of implantation. Therefore, the inspection of organ tissue by attendant physicians or personnel is not possible and only a low degree of sterility control is available.

Therefore, a long standing need has existed to provide a unique transportation apparatus and system for body organs which permit the hypothermic transport of donor organs and which will permit a high degree of sterility control, as well as for visual inspection of organ tissue during transportation and particularly immediately prior to a transplantation procedure.

SUMMARY OF THE INVENTION

Accordingly, the above problems and difficulties are obviated by the present invention which provides a novel disposable medical product taking the form of a hypothermic organ transport container which comprises an inner container holding a quantity of organ preservation medium into which the organ is suspended during transportation. An access lid is threadably engageable with one end of the inner container, permitting access to and from the interior of the inner container. An outer container of larger size than the inner container is provided into which the inner container is held so that a thermoregulatory chamber is defined between the external surface of the inner container and the internal surface of the outer container. This chamber is occupied by a suitable thermoregulatory fluid so as to maintain the suspended organ in the inner container at a proper temperature for the protection of tissues and vascular conditioning. A level marker is provided on the outer container indicating the thermoregulatory fluid level so that insertion of the inner container into the outer container will displace the thermoregulatory fluid about the entire inner container. An exhaust port is provided on the outer container for eliminating excess air within the outer container so that regulatory fluid is displaced to the proper level. A screw cap is placed on the outer container to maintain the inner container in a storage position and sealing means are provided for sealing the regulatory fluid within the outer container as well as for closing the exhaust port.

Preferably, the sidewalls of the inner and outer containers are composed of a transparent material so that visual inspection of the suspended organ within the inner container can be made exteriorly of the apparatus.

Therefore, it is among the primary objects of the present invention to provide a novel hypothermic organ transport apparatus which is useful for the hypothermic transport of donor organs useful in transplantation.

Another object of the present invention is to provide a hypothermic organ transport container which is disposable and which maintains proper temperature of enclosed organ tissues during transport through the use of a thermoregulatory property of a fluid surrounding the organ.

Another object of the present invention is to provide a disposable medical product for hypothermic transport of donor organs, permitting the suspension of the organ in a protective fluid and which incorporates a pair of coaxially disposed containers having pliable sidewalls so that any external pressure applied is equally distributed throughout the fluid of the container, thereby protecting the organ from pressure injury during transport.

Another object of the present invention is to provide a novel container for holding body organs which allows for sterile isolation of the organ and that provides a high degree of sterility control.

Still a further object of the present invention is to provide a novel hypothermic organ transport container which allows for good visual examination of both organ tissue and accompanying vasculature and wherein a thermoregulatory property of liquid surrounding the organ permits some degree of magnification during inspection.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
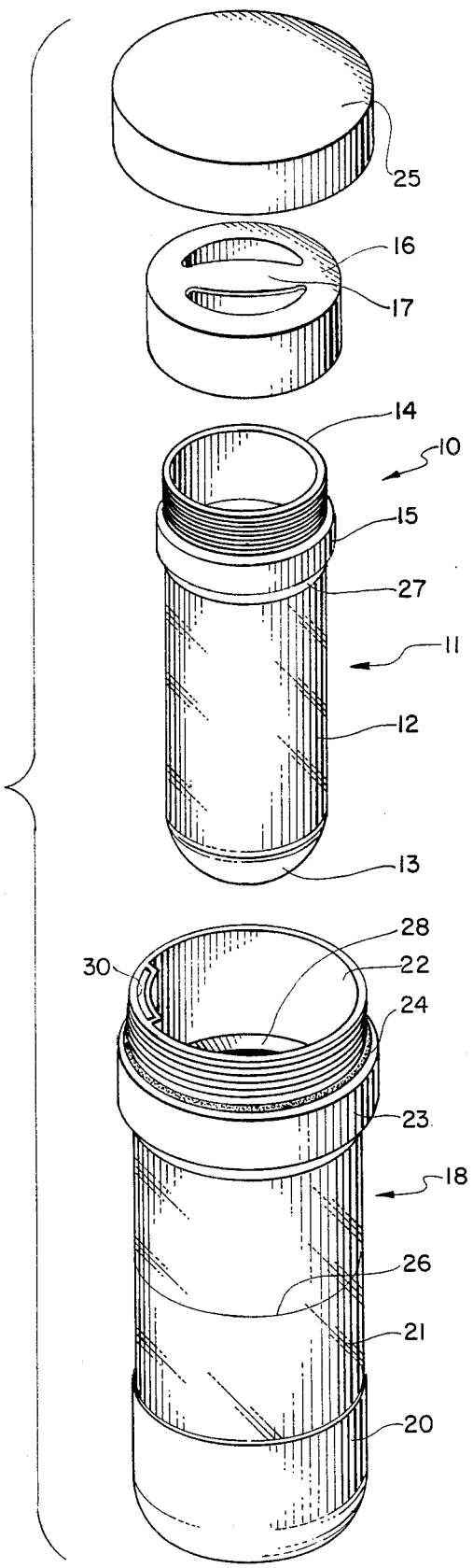
FIG. 1 is an exploded perspective view of the novel hypothermic organ transport apparatus of the present invention.

Referring to FIG. 1, the novel hypothermic organ transport apparatus of the present invention is illustrated in the general direction of arrow 10 which includes an inner container 11 into which a selected body organ is placed intended to be transported or stored. The apparatus is a disposable medical product specifically designed for the hypothermic transport of donor organs useful in the medical procedure of transplantation. The organ intended to be transported is suspended in a suitable preservation medium within the interior of the inner container 11. One form of medium may be a eurocollins solution. The inner container 11 includes a flexible sidewall bag indicated by numeral 12, having a closed end 13 and an opposite open end which is suitably carried on a rigid threaded collar 14 by means of a retaining ring 15. The preservation medium is initially placed into the thin-walled and flexible bag 12 so that the medium surrounds the organ being transported. The inner container includes a lid 16 that is in threadable engagement with the collar 14 so as to seal the contents of the bag and maintain sterility. The lid 16 includes a handle 17 that may be readily grasped by the hands of the user for placing the lid on the collar 14 or for removing the lid therefrom.

The inner container 11 is introduced into a storage chamber of an outer container 18, taking the form of a rigid bottom 20 secured to one end of a thin-walled sleeve 21. The end of the sleeve 21 from its end attached to the bottom 20 is secured to a rigid collar 22 by means of a retaining ring 23 so that sealed securement is produced. An "O"-ring seal 24 is sealingly disposed between the upper end of retainer 23 and the underside of a tap 25 which is threadably engaged with the collar 22.

It is of import to note that preparatory to insertion of the inner container into the storage compartment of the outer container, the storage compartment is partially occupied by a thermoregulatory fluid which will properly maintain the temperature of the organ tissues within a suitable temperature range. When the thermoregulatory fluid is poured into the outer container, the fluid will rise to a level indicated by a marker or scoreline 26 which encircles the sleeve 21. Once this level has been reached, pouring can stop since insertion of the inner container 11 will displace the thermoregulatory fluid so that the fluid will substantially occupy the entire inner storage compartment of the sleeve 21. Therefore, once the inner container 11 has been placed within the outer container, an annular chamber is defined between the exterior surface of the inner container and the inner surface of the outer container into which the thermoregulatory fluid is disposed. Normal saline solution may be used.

It is also to be noted that mounting means for suspending the bag 12 in the storage compartment of the outer container is provided which is indicated by conformal tapered or angular surfaces 27 and 28 carried on the respective collars 14 and 22. Once the container 11 has been introduced into the storage compartment of the outer container 18, the tapered surface 27 will engage with the tapered surface 28 so that the bag 12 is fully suspended within the storage compartment of container 18 and wherein the bottom 13 may be free-floating or may be supported on the bottom 20.

An exit port 30 is provided on the inside of collar 22 which is open-ended so that excess thermoregulatory fluid may be poured out of the storage compartment in a convenient and controlled manner. However, when the cap 25 has been threadably received onto the collar 22, sealing takes place so that the entire assemblage is sealed and leakage is prevented.

Figures 2, 3:
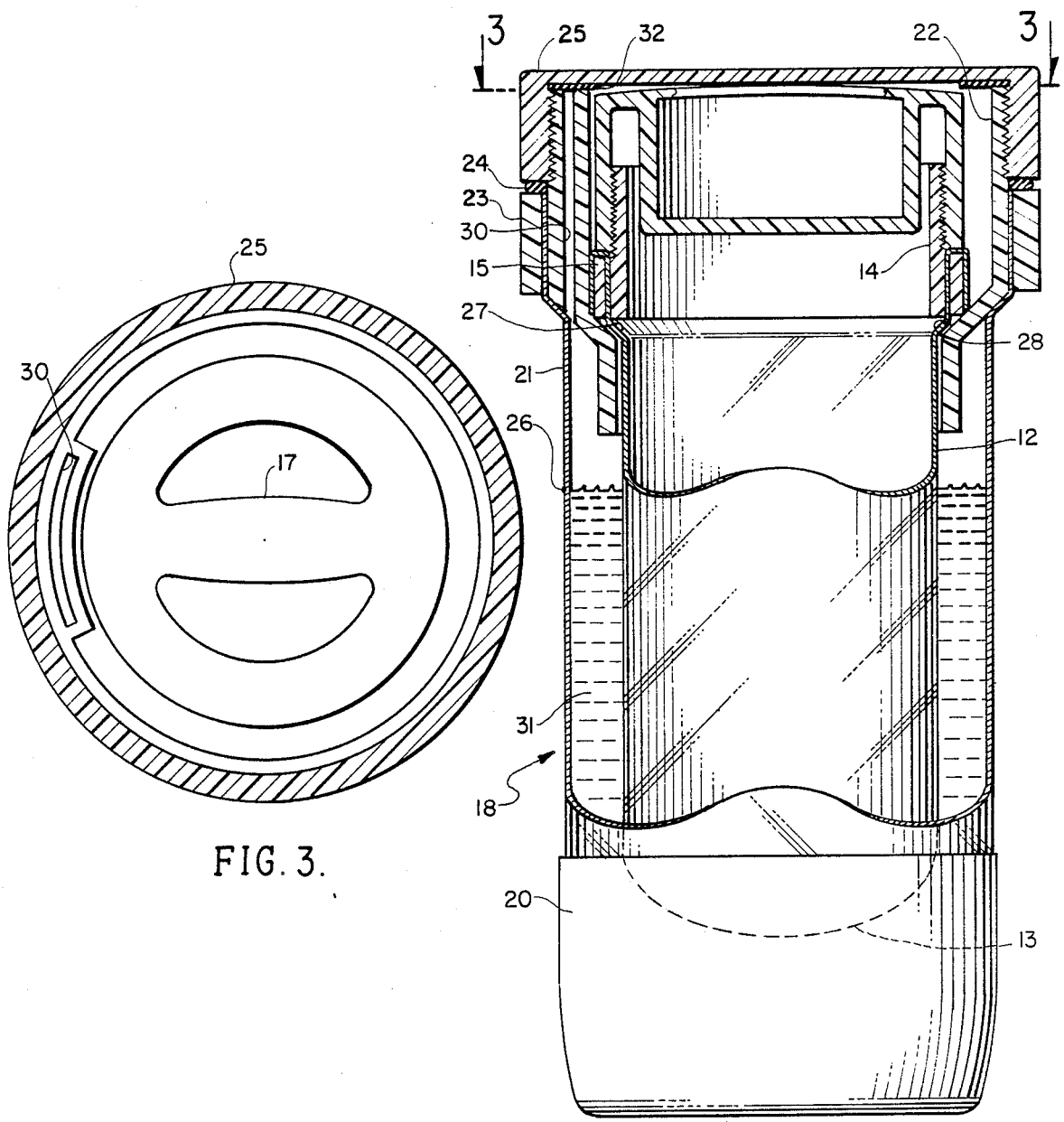
FIG. 2 is a side elevational view, partially broken away, of the transport apparatus shown in FIG. 1 illustrating the component parts thereof.
FIG. 3 is a transverse cross-sectional view of the transport apparatus shown in FIG. 2 as taken in the direction of arrows 3—3 thereof.

Referring now to FIGS. 2 and 3, it can be seen that the flexible bag 12 is disposed within the storage compartment on the interior of the outer container 18. The thermoregulatory fluid is indicated by numeral 31 and is illustrated at the filling level indicated by the marker 26. The thermoregulatory property of the fluid maintains proper temperature of the organ tissues during transport which is approximately 4° centigrade. It is also to be noted that the sidewall of the bag 12 and of the sleeve 21 is relatively thin and transparent. The transparency of the sidewalls permits preoperative visual examination of the organ, of both organ tissue and accompanying vasculature. The fluid 31 provides some degree of magnification; however, it is to be understood that the fluid is also transparent so as not to interfere with the visual examination. Furthermore, the flexibility of the sleeve 26 and the wall of the bag 12 provides a protection to the transported organ since the organ is suspended in a preservation medium or fluid and any pressure applied exteriorly is equally distributed throughout the fluid of the container, thereby protecting the organ from pressure injury during transport.

The O-ring 24 is illustrated as being sealed between the opposing surfaces of the retainer 23 and the cap 25. A flat seal 32 is provided on the underside of the cap 25 so as to close off the open end of the exhaust port 30. Therefore, complete sealing of the apparatus is assured.

In view of the foregoing, it can be seen that the disposable medical apparatus of the present invention provides for a hypothermic transport of donor organs. The apparatus and system is comprised of a fluid-walled container encasing an inner chamber in which the organ is suspended in a suitable preservation medium. The inner container is introduced into the storage compartment of an outer container which contains a suitable thermoregulatory fluid and sealing means are provided for holding the inner container coaxial with respect to the outer container and so that the fluids will not escape or spill. The apparatus and system allows for the sterile isolation of the transported organ and provides a high degree of control. Therefore, the apparatus provides consistency in transport procedure and technique with respect to temperature control, volume of preservation medium and the like. The present system is particularly adapted to the transport of kidneys, adult and pediatric heart and pancreas.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A hypothermic organ transport apparatus comprising:
   an inner container for storing a body organ;
   an outer container for insertably receiving said inner container in spaced coaxial relationship;
   a preservation medium carried in said inner container in communication with said body organ;
   a thermoregulatory fluid substantially surrounding said inner container and occupying the space between said coaxial inner and outer containers;
   sealing means operably securing said inner container with said outer container to maintain said preservation medium and said thermoregulatory fluid in their respective locations;

mounting means detachably coupling said inner container with said outer container to maintain said inner container in a suspended and coaxial position with respect to said outer container;

marker means carried on said outer container indicating level of said thermoregulatory fluid within said outer container preparatory to insertion of said inner container;

an open-ended port disposed on the inside of said outer container selectively in communication exteriorly thereof for discharging thermoregulatory fluid to the level of said marker means;

said inner container includes an elongated bag composed of transparent material and said outer container includes a cylindrical sleeve about said inner container bag in spaced relationship composed of transparent material;

said outer container sleeve and said inner container bag are of flexible thin-walled construction; and said inner container downwardly depends within said outer container from said mounting means in close communication with said thermoregulatory fluid.

2. The invention as defined in claim 1 wherein:

said inner container is an integral sealed container;

said mounting means includes an expanded ring on its exterior surface; and said outer container includes an exposed mounting surface conformal with and engageable with said ring whereby said inner container suspends therefrom and is held coaxial therewith.

3. The invention as defined in claim 2 wherein:

said open-ended port conducts air from said outer container exteriorly in response to insertion of inner container with said outer container so that said regulatory fluid substantially occupies the space between said inner and outer containers.

* * * * *